United States Patent
Ghanem et al.

(10) Patent No.: US 7,496,408 B2
(45) Date of Patent: Feb. 24, 2009

(54) ELECTRODES ARRAY FOR A PACEMAKER

(75) Inventors: Raja N. Ghanem, Minneapolis, MN (US); Walter H. Olson, North Oaks, MN (US)

(73) Assignee: Medtronic, Inc., Minneapolis, MN (US)

( * ) Notice: Subject to any disclaimer, the term of this patent is extended or adjusted under 35 U.S.C. 154(b) by 362 days.

(21) Appl. No.: 11/004,498

(22) Filed: Dec. 3, 2004

(65) Prior Publication Data

US 2006/0122649 A1 Jun. 8, 2006

(51) Int. Cl.
*A61N 1/04* (2006.01)
(52) U.S. Cl. .............................. 607/115; 607/9; 607/119
(58) Field of Classification Search .................. 607/2, 607/4–5, 116–117, 119, 122, 7, 9–11, 63, 607/68, 70, 72, 74, 115, 129, 142; 600/372–374, 600/377, 381, 382, 393
See application file for complete search history.

(56) References Cited

U.S. PATENT DOCUMENTS

| | | | | |
|---|---|---|---|---|
| 3,727,616 A | | 4/1973 | Lenzkes | 128/422 |
| 3,893,461 A | * | 7/1975 | Preston | 607/17 |
| 4,166,470 A | * | 9/1979 | Neumann | 607/33 |
| 4,349,030 A | | 9/1982 | Belgard et al. | 128/419 PG |
| 4,352,360 A | | 10/1982 | King | 128/786 |
| 4,388,930 A | | 6/1983 | De Bellis | 128/419 PS |
| 4,587,970 A | | 5/1986 | Holley et al. | 128/419 PG |
| 4,727,380 A | | 2/1988 | Miura et al. | 346/108 |
| 4,727,877 A | | 3/1988 | Kallok | 128/419 D |
| 4,800,883 A | | 1/1989 | Winstrom | 129/419 D |
| 4,830,006 A | | 5/1989 | Haluska et al. | 128/419 PG |
| 4,848,352 A | * | 7/1989 | Pohndorf et al. | 600/374 |
| 4,953,551 A | | 9/1990 | Mehra et al. | 128/419 D |
| 5,018,522 A | | 5/1991 | Mehra | 128/419 PG |
| 5,095,903 A | | 3/1992 | DeBellis | 128/419 P |
| 5,111,812 A | * | 5/1992 | Swanson et al. | 607/2 |
| 5,117,824 A | | 6/1992 | Keimel et al. | 128/419 D |
| 5,163,427 A | | 11/1992 | Keimel | 128/419 D |

(Continued)

FOREIGN PATENT DOCUMENTS

WO     WO 93/23113 A1     11/1993

(Continued)

OTHER PUBLICATIONS

U.S. Appl. No. 11/037,123, filed Jan. 18, 2005, entitled "Method and Apparatus for Arrhythmia Detection in a Medical Device" to Mitrani et al.

(Continued)

*Primary Examiner*—Carl H Layno
*Assistant Examiner*—Jessica Reidel
(74) *Attorney, Agent, or Firm*—Michael C Soldner

(57) ABSTRACT

A cardiac pacemaker and method of its use. The pacemaker is provided with a pacing electrode array configured for location at a left anterior portion of a patient's thorax between the patients third and sixth ribs, outside the patient's thoracic cavity. The pacing electrode array includes multiple pacing electrodes and preferably includes one or more steering electrodes for configuring the electrical field produced by delivery of pacing pulses to avoid unwanted nerve and muscle stimulation while allowing cardiac stimulation. The electrode array may be located subcutaneously, submuscularly or on the patient's skin.

5 Claims, 6 Drawing Sheets

U.S. PATENT DOCUMENTS

| | | | | |
|---|---|---|---|---|
| 5,188,105 A | | 2/1993 | Keimel | 128/419 D |
| 5,300,106 A | | 4/1994 | Dahl et al. | 607/119 |
| 5,360,442 A | | 11/1994 | Dahl et al. | 607/129 |
| 5,370,665 A | * | 12/1994 | Hudrlik | 607/9 |
| 5,466,247 A | | 11/1995 | Scheiner et al. | 607/48 |
| 5,509,924 A | | 4/1996 | Paspa et al. | 607/5 |
| 5,524,632 A | | 6/1996 | Stein et al. | 128/733 |
| 5,603,732 A | | 2/1997 | Dahl et al. | 607/129 |
| 5,662,689 A | | 9/1997 | Elsberry et al. | 607/5 |
| 5,752,977 A | | 5/1998 | Grevious et al. | 607/32 |
| 5,782,882 A | | 7/1998 | Lerman et al. | 607/10 |
| 5,800,465 A | * | 9/1998 | Thompson et al. | 607/9 |
| 5,814,076 A | | 9/1998 | Brownlee | 607/9 |
| 5,817,131 A | * | 10/1998 | Elsberry et al. | 607/5 |
| 5,895,416 A | * | 4/1999 | Barreras et al. | 607/62 |
| 5,904,711 A | | 5/1999 | Flom et al. | 607/129 |
| 5,999,857 A | | 12/1999 | Weijand et al. | 607/60 |
| 6,006,138 A | * | 12/1999 | Don Michael | 607/124 |
| 6,091,989 A | | 7/2000 | Swerdlow et al. | 607/5 |
| 6,438,418 B1 | | 8/2002 | Swerdlow et al. | 607/5 |
| 6,505,078 B1 | * | 1/2003 | King et al. | 607/67 |
| 6,512,940 B1 | | 1/2003 | Brabec et al. | 600/374 |
| 6,711,442 B1 | | 3/2004 | Swerdlow et al. | 607/63 |
| 6,718,628 B2 | | 4/2004 | Munshi | 29/825 |
| 6,721,597 B1 | | 4/2004 | Bardy et al. | 607/4 |
| 6,763,268 B2 | | 7/2004 | MacDonald et al. | 607/9 |
| 7,047,084 B2 | * | 5/2006 | Erickson et al. | 607/116 |
| 2001/0034539 A1 | | 10/2001 | Stadler et al. | 607/14 |
| 2002/0035377 A1 | | 3/2002 | Bardy et al. | 607/4 |
| 2002/0035378 A1 | | 3/2002 | Bardy et al. | 607/4 |
| 2002/0035379 A1 | | 3/2002 | Bardy et al. | 607/4 |
| 2002/0035381 A1 | | 3/2002 | Bardy et al. | 607/4 |
| 2002/0042634 A1 | | 4/2002 | Bardy et al. | 607/36 |
| 2002/0052636 A1 | | 5/2002 | Bardy et al. | 607/129 |
| 2002/0068958 A1 | | 6/2002 | Bardy et al. | 607/5 |
| 2002/0072773 A1 | | 6/2002 | Bardy et al. | 607/5 |
| 2002/0082658 A1 | | 6/2002 | Heinrich et al. | 607/9 |
| 2002/0099402 A1 | | 7/2002 | Buckman et al. | 606/185 |
| 2002/0103510 A1 | | 8/2002 | Bardy et al. | 607/5 |
| 2002/0107547 A1 | | 8/2002 | Erlinger et al. | 607/5 |
| 2002/0107548 A1 | | 8/2002 | Bardy et al. | 607/5 |
| 2002/0107549 A1 | | 8/2002 | Bardy et al. | 607/5 |
| 2002/0107559 A1 | | 8/2002 | Sanders et al. | 607/129 |
| 2002/0133187 A1 | | 9/2002 | Buckman et al. | 606/185 |
| 2003/0045904 A1 | | 3/2003 | Bardy et al. | 607/4 |
| 2003/0078633 A1 | | 4/2003 | Firlik et al. | 607/46 |
| 2003/0114906 A1 | | 6/2003 | Booker, III et al. | 607/122 |
| 2003/0220676 A1 | * | 11/2003 | Helland | 607/122 |
| 2004/0116793 A1 | * | 6/2004 | Taimisto et al. | 600/374 |

FOREIGN PATENT DOCUMENTS

| | | |
|---|---|---|
| WO | WO 96/36395 A1 | 11/1996 |
| WO | WO 02/00102 A2 | 1/2002 |
| WO | WO 02/24275 A2 | 3/2002 |
| WO | WO 02/058573 A1 | 8/2002 |
| WO | WO 03/018110 A2 | 3/2003 |
| WO | WO 03/018111 A2 | 3/2003 |
| WO | WO 03/018112 A2 | 3/2003 |
| WO | WO 03/018127 A2 | 3/2003 |
| WO | WO 03/018130 A2 | 3/2003 |
| WO | WO 03/039656 A1 | 5/2003 |
| WO | WO 2004/043919 A1 | 5/2004 |

OTHER PUBLICATIONS

Sweeney et al., "A Nerve Cuff Technique for Selective Excitation of Peripheral Nerve Trunk Regions," *IEEE Trans on Biomedical Eng.*, vol. 37, No. 7, p. 706-715 (Jul. 1990).

* cited by examiner

ELECTRODES ARRAY FOR A PACEMAKER

FIELD OF THE INVENTION

This invention relates generally to pacemakers and pacemaker-cardioverter-defibrillators (ICDs) and more particularly to pacemakers and ICDs that are implantable subcutaneously or submuscularly entirely outside the thoracic cavity with minimal surgical intrusion into the body of the patient.

BACKGROUND OF THE INVENTION

Interest has recently increased in the development of implantable defibrillators that may be inserted entirely subcutaneously or sub-muscularly, having no leads or electrodes within the thoracic cavity. The elimination of transvenous or epicardial leads is believed likely to allow for implant of the devices by a wider range of physicians, in some cases at a lower cost than traditional implantable cardio defibrillators (ICDs). Such devices, are therefore believed to offer the opportunity for increased levels of use, particularly for prophylactic implant. US Application Publication Nos. 2002/0042634, 2002/00068958 and 2002/0035377 to Bardy et al., are exemplary of current thinking with regard to such subcutaneous ICDs. Additional subcutaneous ICDs are disclosed in US Application Publication No. 20020082658 by Heinrich et al. and PCT publication WO/04043919A2 by Olson. All of the above cited applications and publications are incorporated herein by reference in their entireties.

The above-referenced Bardy et al. applications disclose subcutaneously implanted ICD IPGs that are coupled with at least one cardioversion/defibrillation lead. In certain embodiments, the ICD IPG has a conventional configuration having a can electrode that functions as one cardioversion/defibrillation electrode and is implanted subcutaneously anterior or posterior to the heart. The cardioversion/defibrillation lead is tunnelled subcutaneously under the skin and around the thorax to locate the lead supported cardioversion/defibrillation electrode posterior or anterior to the heart, respectively. In certain embodiments, two cardioversion/defibrillation leads that are electrically connected together are tunnelled subcutaneously under the skin and around the thorax to locate the two cardioversion/defibrillation electrodes apart from one another and posterior or anterior to the heart, respectively. Electrical sensing of the cardiac electrical activity is accomplished across two sense electrodes displaced apart from one another on the IPG housing or on the lead. Cardioversion/defibrillation shocks are delivered across the thorax between the cardioversion/defibrillation electrodes on the ICD housing and the lead. It is also asserted that cardiac pacing pulses can be applied to the heart across the cardioversion/defibrillation electrodes on the ICD housing and the lead. In certain embodiments, the ICD housing is shaped in an elongated, thin, narrow shape to approximate and conform to the curvature of the thorax for cosmetic reasons and in some cases to fit between the ribs, e.g., between the fourth and fifth ribs. In some such embodiments, the ICD may have no associated subcutaneous lead and may have both cardioversion/defibrillation electrodes mounted to the ICD housing.

While the above-cited applications by Bardy et al generally propose that pacing be done using the large surface area cardioversion/defibrillation electrodes, the Olson publication proposes that pacing may be accomplished using two smaller electrodes. One of these electrodes may be located on each of two separate device housings that are coupled to one another by a subcutaneous lead. Alternatively, one of the pacing electrodes may be located on the subcutaneous lead.

Like transthoracic pacing, for example as disclosed in U.S. Pat. Nos. 4,349,030, and 5,018,522, subcutaneous pacing has the potential to cause discomfort to the patient, as well as phrenic nerve and/or muscular stimulation, including direct diaphragmatic stimulation. This drawback may limit the use of subcutaneous pacing therapies, including anti-tachycardia, anti-bradycardia or post-shock pacing, in some patients.

SUMMARY OF THE INVENTION

The present invention is intended to reduce or eliminate undesirable effects of subcutaneous pacing such as those discussed above. In some preferred embodiments, the invention takes the form of an ICD having a subcutaneous pacing electrode array, adapted for implant with all electrodes located close to the heart. In these embodiments, the pacing electrodes are separate from the large surface area electrodes used for delivery of cardioversion and defibrillation pulses. In some of these embodiments, the pacing electrode array may be located on a subcutaneous lead or leads, coupled to the ICD housing and extending to a desired implant site, i.e. in the anterior thorax, overlying the heart, slightly left of the sternum and between the third and sixth ribs. In other of these embodiments, the pacing electrode array may be located on the ICD housing, which preferably is shaped to facilitate implant at the desired site referred to above.

In other embodiments of the invention, the invention may take the form of a permanently or temporarily implantable subcutaneous pacemaker (IPG), lacking cardioversion and defibrillation capabilities. As in the ICD based embodiments discussed above, the electrode array may be located on either the IPG housing or on a lead or leads extending from the IPG housing. In yet other embodiments, the invention may take the form of a temporarily implanted subcutaneous pacing lead coupled to an external temporary pacemaker. While the invention is directed primarily toward subcutaneous pacing, particularly in those embodiments in which the pacing electrode array is located on a lead, the invention may also have applicability to transthoracic pacing. In such cases, the lead carrying the pacing electrode array may be applied to the skin external to the desired implant site described above and coupled to an external transthoracic pacemaker. In the context of automated external defibrillators, the invention may also be useful in post-shock trans-thoracic pacing.

The pacing electrode array of the present invention includes at least two electrodes, and in many embodiments includes three or more electrodes. In a first set of embodiments, the array takes the form of two or more concentric pacing electrodes. In a second set of embodiments the array includes three pacing electrodes arranged linearly to form a shielded dipole. In conjunction with either the first or second set of embodiments, a steering electrode, laterally offset from the shielded dipole or concentric electrodes, may be provided in order to steer the electrical field generated by the pacing electrodes. In a third set of embodiments, three or more concentric or non-concentric electrodes are provided, and may be programmably coupled to a pacemaker to produce an electrical stimulation field having desired characteristics.

In all of the embodiments discussed above, the electrodes within the array are smaller than would typically be used for cardioversion or defibrillation. For example, the individual electrodes are preferably all be about one square centimeter in area or less. In order that the array may be entirely located at the desired implant site as described above, it is preferable that the array extend over a maximum dimension of no more than about 12 cm, more preferably no more than approximately 8 cm.

While the pacing electrode arrays described below are coupled to their associated pacing pulse generators by means of conventional continuous metallic or carbon conductors, it is believed that the invention may also be useful in a device system in which the electrode array is coupled to a remote device by radio frequency, for example as in U.S. Pat. Nos. 4,388,930 and 5,095,903 issued to DeBellis, U.S. Pat. No. 3,727,616 issued to Lenzkes, by fiber-optic cables as in U.S. Pat. No. 6,763,268 issued to MacDonald et al, all incorporated herein by reference in their entireties, or other by interconnection method.

Finally, in some embodiments, additional pain control techniques might be added. These techniques may include delivery of neurostimulation, delivery of analgesics and use of the technique of prepulse inhibition to reduce discomfort associated with subcutaneous pacing.

BRIEF DESCRIPTION OF THE DRAWINGS

These and other advantages and features of the present invention will be appreciated as the same becomes better understood by reference to the following detailed description of the preferred embodiment of the invention when considered in connection with the accompanying drawings, in which like numbered reference numbers designate like parts throughout the figures thereof, and wherein.

DETAILED DESCRIPTION OF THE PREFERRED EMBODIMENTS

Figure 1:
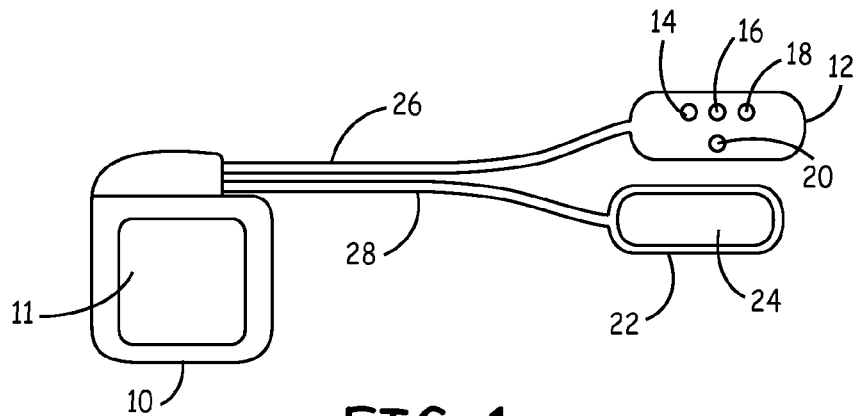
FIG. 1 illustrates a first embodiment of the invention, taking the form of an ICD or IPG coupled to a pacing electrode array located on a subcutaneous lead.

FIG. 1 illustrates a first embodiment of the present invention, having a first embodiment of a pacing electrode array. An implantable medical device, such as an ICD 10 is shown coupled to two subcutaneous leads 26 and 28. Lead 28, like the other leads discussed below, has an elongated lead body carrying conventional, mutually insulated conductors, each coupled to one of the electrodes on the lead. At its distal end is an insulated electrode head or pad 22, carrying an exposed large surface area electrode 24, intended to face inward as implanted. An uninsulated portion 11 of the conductive housing of ICD 10, also intended to face inward as implanted, and electrode 24 are employed as high voltage cardioversion/defibrillation electrodes. An additional cardioversion/defibrillation electrode may optionally be located along the length of either lead. Lead 26 also has an insulated electrode head or pad 12, carrying an array of exposed pacing electrodes 14, 16, 18 and 20, also intended to face inward as implanted. One or more of these electrodes may also be employed to sense cardiac depolarizations. The conductive housing of ICD 10 may also be employed in conjunction with one or more of electrodes 14, 16, 18 or 20 to sense cardiac depolarizations. Electrode pad 12 is preferably implanted at the preferred implant site over the third, fourth or fifth intercostal space, slightly left of the midline of the patients sternum, as discussed above, placing all pacing electrodes in close proximity to the heart. Electrode 24 is preferably placed adjacent to electrode pad 12 but may be placed remote from it. Like the electrode arrays discussed below in conjunction with FIGS. 2-11, the electrodes within the pacing electrode array are preferably no more than about two square centimeters in area, more preferably no more than about one square centimeter in area. The pacing electrode array preferably extends over a maximum dimension of no more than about twelve centimeters, more preferably no more than about eight centimeters.

As illustrated, the electrode array includes electrodes 14, 16, 18 and 20 may be selectably configured as a shielded dipole (tripolar stimulation) including linearly arranged electrodes 14, 16 and 18, with laterally offset electrode 20 serving as a field steering electrode, much as described in the article: "A Nerve cuff Technique for Selective Excitation of Peripheral Nerve Trunk Regions", Sweeney, et al., IEEE Trans on Biomedical Engineering, 37(7), July 1990, pp 706-715, incorporated herein by reference in its entirety. For example, outer electrodes 14 and 18 may serve as positive electrodes, with central electrode 16 serving as the negative electrode. This tripolar design serves to concentrate the pacing pulse field in the region between electrodes 14 and 18, with the intended result of reducing undesired muscle and nerve stimulation. Electrode 20 serves as a steering electrode and is also a positive electrode. The voltage drop between electrodes 16 and 20 may be adjusted to steer the electrical field to extend more or less away from the region between electrodes 14 and 18, during delivery of the pacing pulse. While as illustrated, only one steering electrode is provided, in alternative embodiments, multiple steering electrodes or elongated steering electrodes may be provided. The energy delivered between the central electrode 16 and the steering electrode 20 may be below the pacing threshold or above it. In practice, the physician preferably adjusts the voltage between electrodes 16, and 20, independent of the voltage between electrode 16 and electrodes 14 and 18, in order to minimize the level of energy needed to pace the heart and in order to minimize undesirable nerve and muscle stimulation. Adjustment is made as a function of the patient's response to delivered pacing pulses and the ability of the pulses to capture the heart.

The electrodes in the pacing electrode array of FIG. 1, like those of the Figures discussed below, may be conventional metallic pacing electrodes. Alternatively, it is believed that some reduction in the pain associated with subcutaneous pacing may be available through the use of non-metallic pacing electrodes, such as carbon pacing electrodes, DCD electrodes or conductive polymer coated electrodes as in U.S. Pat. No. 6,718,628 issued to Munshi, or U.S. Pat. No. 4,352,360 issued to King, both incorporated herein by reference in their entireties. In those embodiments of the invention in which the pacing electrode array is located on the surface of the skin, non-metallic electrodes corresponding to available transcutaneous pacing electrodes, although as discussed above preferably much smaller, may also be employed.

Although the pacing electrode array is illustrated as separate from high voltage electrode 24, they might optionally all be placed on a single lead, for example, with electrode 24 taking the form of a coiled electrode mounted along lead 26 or encircling electrode pad 12. If the invention is embodied in the form of a subcutaneous pacer only, lead 28 would be eliminated. An exemplary embodiment of an ICD corresponding to ICD 10 is described below in conjunction with FIGS. 13-15. Further, while leads 26 and 28, like the leads discussed below, are shown with pacing electrodes located on the inward facing side of an insulative electrode pad, it should be understood that in some embodiments, these structures can be replaced with full or partial ring electrodes, mounted about a generally cylindrical lead body, or with other electrode configurations.

Figure 2:
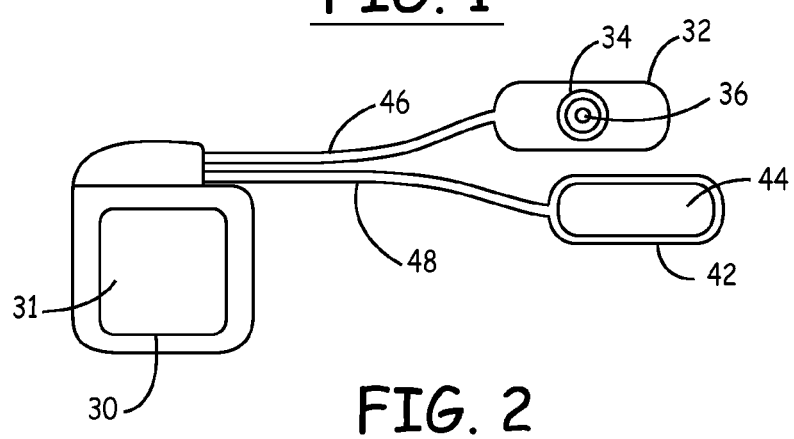
FIG. 2 illustrates a second embodiment of the invention, taking the form of an ICD or IPG coupled to a concentric pacing electrode array located on a subcutaneous lead.

FIG. 2 illustrates a second embodiment of the present invention, having a second embodiment of an electrode array. An ICD 30 is shown coupled to two subcutaneous leads 46 and 48. Lead 48 has an insulated electrode head or pad 42, carrying an exposed large surface area electrode 44. An uninsulated portion 31 of the conductive housing of ICD 30 and electrode 24 are employed as high voltage cardioversion/defibrillation electrodes. An additional cardioversion/defibrillation electrode may optionally be located along the length of either lead. Lead 46 also has an insulated electrode head or pad 32, carrying an exposed array of concentric pacing electrodes including outer ring electrode 34 (typically positive) and central electrode 36 (typically negative). This configuration, like that of the array of FIG. 1, is intended to concentrate the field in the area between the electrodes, reducing the chances of undesirable nerve or muscle stimulation. One or more of these electrodes may also be employed to sense cardiac depolarizations. The conductive housing of ICD 30 may also be employed in conjunction with one or more of electrodes 34 or 36 to sense cardiac depolarizations. Electrode pad 32 is preferably implanted at the preferred implant site discussed above. Electrode 44 is preferably placed adjacent to electrode pad 32 but may be placed remote from it. Like the pacing electrodes of the embodiment illustrated in FIG. 1, one or more of the pacing electrodes may also be used to sense cardiac depolarizations.

As with the embodiment of FIG. 1, high voltage electrode 44, might optionally be placed on a single lead with electrodes 34 and 36, for example with electrode 44 taking the form of a coiled electrode mounted along lead 46 or encircling electrode pad 32. If the invention is embodied in the form of a subcutaneous pacer only, lead 48 would be eliminated. An exemplary embodiment of an ICD corresponding to ICD 30 is described below in conjunction with FIGS. 13-15.

Figure 3A:
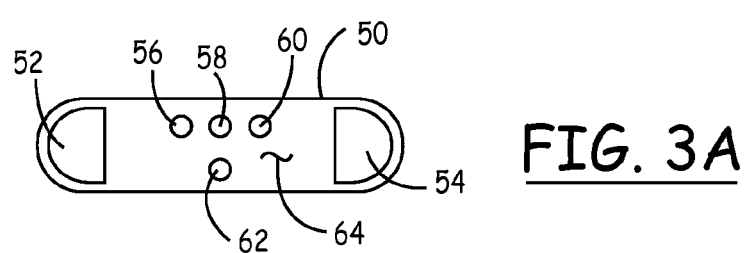
FIG. 3a illustrates a third embodiment of the invention, taking the form of an ICD or IPG having a pacing electrode array as in FIG. 1, located on the device housing.

FIG. 3a illustrates a third embodiment of the present invention. In this embodiment, ICD 50 has no associated leads and carries all electrodes on its housing. The pacing electrode array including electrodes 56, 58, 60 and 62 functions identically to the pacing electrode array of the device of FIG. 1. High voltage cardioversion/defibrillation electrodes 52 and 54 are located on opposite ends of surface 64, intended to be implanted facing inwards, at the desired implant location referred to above. The housing of ICD 50 may be curved to conform to the geometry of the preferred implant site, with inward surface 64 being concave and the opposite outer surface of the ICD being convex. A variety of possible housing configurations are illustrated in the '958 application by Bardy, et al., discussed above. If the invention is embodied in the form of a subcutaneous pacer only, electrodes 52 and 54 would be eliminated.

Figure 3B:
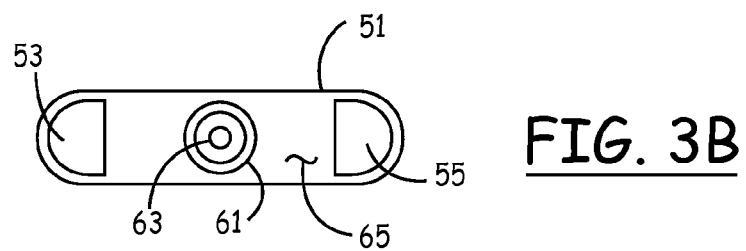
FIG. 3b illustrates a fourth embodiment of the invention, taking the form of an ICD or IPG having a pacing electrode array as in FIG. 2, located on the device housing

FIG. 3b illustrates a fourth embodiment of the present invention. In this embodiment, ICD 51 has no associated leads and carries all electrodes on its housing. The pacing electrode array including electrodes 61 and 63 functions identically to the pacing electrode array of the device of FIG. 2. High voltage cardioversion/defibrillation electrodes 53 and 55 are located on opposite ends of surface 65, intended to be implanted facing inwards, at the desired implant location referred to above. The housing of ICD 51 may be curved to conform to the geometry of the preferred implant site, with inward surface 65 being concave and the opposite outer surface of the ICD being convex. If the invention is embodied in the form of a subcutaneous pacer only, electrodes 53 and 55 would be eliminated. An exemplary embodiment of an ICD corresponding to ICD 51 is described below in conjunction with FIGS. 13-15.

Figure 4:
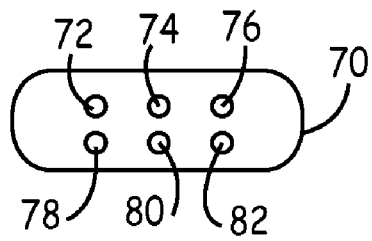
FIG. 4 illustrates a third embodiment of an electrode array according to the present invention.

FIG. 4 illustrates a third embodiment of a pacing electrode array according to the present invention. Electrodes 72, 74, 76, 78, 80 and 82 form a 2×6 array on surface 70. Surface 70 may be either a surface of an IPG or ICD, generally as in FIG. 3, or may be an electrode pad on a subcutaneous lead as in FIGS. 1 and 2. The electrodes in the array may be used in a variety of ways. For example electrodes 72, 74 and 76 may be selectably programmed to form a shielded dipole, as discussed in conjunction with FIG. 1, with one of electrodes 78, 80 and 82 selectably programmed to act as a steering electrode. In this configuration, both the voltage of the steering electrode and its location can be controlled to provide a wider set of available field configurations. Alternatively, the physician can simply select two or more electrodes on surface 70 and pulse voltages to provide a variety of electrical field orientations.

Figure 5:
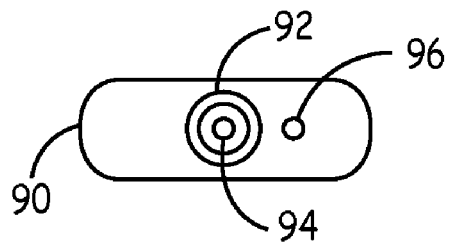
FIG. 5 illustrates a fourth embodiment of an electrode array according to the present invention.

FIG. 5 illustrates a fourth embodiment of a pacing electrode array according to the present invention. Electrodes 92, 94 and 96 are located on surface 90. Surface 90 may be either a surface of an IPG or ICD, generally as in FIG. 3, or may be an electrode pad on a subcutaneous lead as in FIGS. 1 and 2. The electrodes in the array include electrode 92 (typically positive) and electrode 94 (typically negative), which form a concentric pair, along with a field steering electrode 96. Electrode 96 serves as the steering electrode and typically is of the same polarity as electrode 92. As with the embodiment of FIG. 1, the voltage drop between electrodes 94 and 96 is intended to be adjustable independent of the voltage drop between electrodes 92 and 94, to allow the physician to adjust the field distribution.

Figure 6:
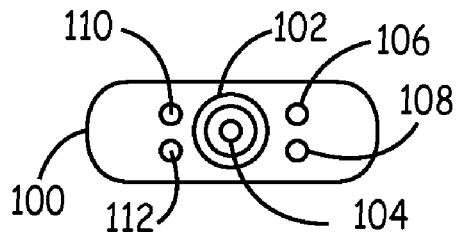
FIG. 6 illustrates a fifth embodiment of an electrode array according to the present invention.

FIG. 6 illustrates a fifth embodiment of a pacing electrode array according to the present invention. Electrodes 102, 104, 106, 108, 110 and 112 are located on surface 100. Surface 100 may be either a surface of an IPG or ICD, generally as in FIG. 3, or may be an electrode pad on a subcutaneous lead as in FIGS. 1 and 2. The electrodes in the array include 102 (typically positive) and 104 (typically negative), which form a concentric pair, along with a field steering electrodes 106, 108, 110 and 112. The steering electrodes may be selectably activated by the physician, and typically are of the same polarity as electrode 102. As with the embodiment of FIG. 1, the voltage drop between electrodes 104 and the selected one or more steering electrodes are intended to be adjustable independent of the voltage drop between electrodes 102 and 104, to allow the physician to adjust the field distribution. In this configuration, both the voltage of the steering electrode or electrodes and their location can be controlled to provide a wider set of available field configurations. Alternatively, the physician can simply select two or more electrodes on surface 100 and their associated pulse voltages to provide a variety of electrical field orientations.

According to the present invention, in the electrode configuration of FIGS. 2, 3b and 6, the area of the outer electrode and central electrode is preferably equal, although the diameter of the outer electrode may vary in size. For example, according to an embodiment of the present invention, the area of both the outer electrode and the central electrode is approximately equal to 20 $mm^2$.

Figure 7:
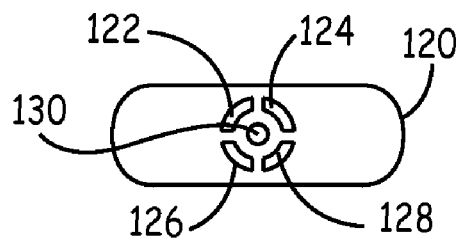
FIG. 7 illustrates a sixth embodiment of an electrode array according to the present invention.

FIG. 7 illustrates a sixth embodiment of an electrode array according to the present invention. Electrodes 122, 124, 126, 128 and 130 are located on surface 120. Surface 120 may be either a surface of an IPG or ICD, generally as in FIG. 3, or may be an electrode pad on a subcutaneous lead as in FIGS. 1 and 2. The electrodes in the array may be used in a variety of ways. For example electrodes 122, 124, 126 and 128 may all be connected in common as positive electrodes with electrode 130 negative, to form a concentric pair, as discussed in conjunction with FIG. 2. Alternatively, one or more of electrodes 122, 124, 126 or 128 may be disabled or programmed to a lower pulse voltage, in order to vary the field distribution and provide field steering. Alternatively, the physician can simply select two or more electrodes on surface 120 and their associated pulse voltages to provide a variety of electrical field orientations.

Figure 8A:
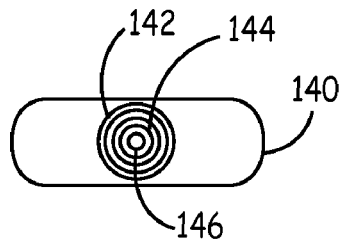
FIG. 8a illustrates a seventh embodiment of an electrode array according to the present invention.

FIG. 8a illustrates a seventh embodiment of a pacing electrode array according to the present invention. Electrodes 142, 144 and 146 are located on surface 140. Surface 140 may be either a surface of an IPG or ICD, generally as in FIG. 3, or may be an electrode pad on a subcutaneous lead as in FIGS. 1 and 2. The electrodes in the array allow for three different concentric pairs to be defined by selecting any two of the electrodes.

Figure 8B:
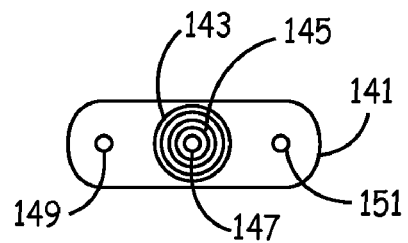
FIG. 8b illustrates an eighth embodiment of an electrode array according to the present invention.

FIG. 8b illustrates a eighth embodiment of a pacing electrode array according to the present invention. Electrodes 143, 145 and 147 are located on surface 141. Surface 141 may be either a surface of an IPG or ICD, generally as in FIG. 3, or may be an electrode pad on a subcutaneous lead as in FIGS. 1 and 2. These three electrodes in the array allow for three different concentric pairs to be defined by selecting any two of the electrodes. In addition, steering electrodes 149 and 151 are provided, which may be used selectably to steer the applied electric field away from the diaphragm.

Figure 9:
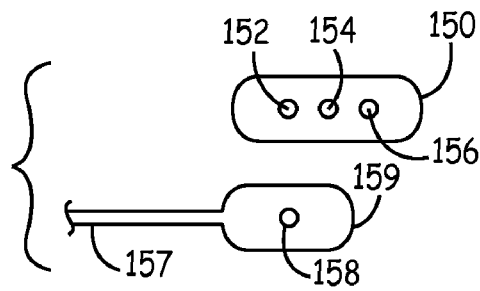
FIG. 9 illustrates a ninth embodiment of an electrode array according to the present invention.

FIG. 9 illustrates a ninth embodiment of a pacing electrode array according to the present invention. Electrodes 152, 154 and 156 are located on surface 150. Surface 150 may be either a surface of an IPG or ICD, generally as in FIG. 3, or may be an electrode pad on a subcutaneous lead as in FIGS. 1 and 2. Electrode 158 is located on an electrode pad 159 of an implantable lead 157, and may be positioned as desired with regard to electrodes 152, 154 and 156. In one configuration, electrodes 152, 154 and 156 may be selectably programmed to form a shielded dipole as discussed above, with electrode 158 serving as a steering electrode. In this configuration, both the voltage of the steering electrode and its location can be controlled to provide a wider set of available field configurations. Alternatively, the physician can simply select two or more electrodes on surface 150 and pad 159 and their associated pulse voltages to provide a variety of electrical field orientations. According to the present invention, additional steering electrodes could be located on pad 159 or on surface 150 so that the number of pacing electrodes and steering electrodes that are provided are selected to maximize capture of the heart and minimize muscle and nerve innervation.

Figure 10:
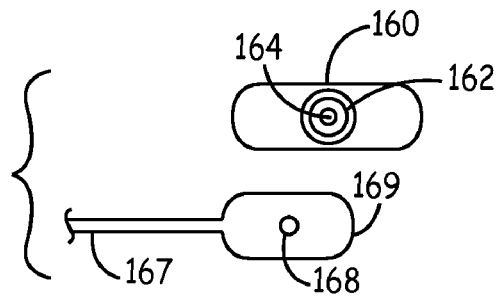
FIG. 10 illustrates an tenth embodiment of an electrode array according to the present invention.

FIG. 10 illustrates a tenth embodiment of a pacing electrode array according to the present invention. Electrodes 162 and 164 are located on surface 160. Surface 160 may be either a surface of an IPG or ICD, generally as in FIG. 3, or may be an electrode pad on a subcutaneous lead as in FIGS. 1 and 2. Electrode 168 is located on an electrode pad 169 of an implantable lead 167, and may be positioned as desired with regard to electrodes 162 and 164. Electrodes 162 and 164 form a concentric pair as discussed above, with electrode 168 serving as a steering electrode. In this configuration, both the voltage of the steering electrode and its location can be controlled to provide a wider set of available field configurations. Alternatively, the physician can simply select two or more electrodes on surface 160 and pad 169 and their associated pulse voltages to provide a variety of electrical field orientations.

Figure 11:
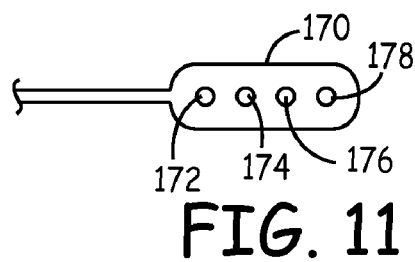
FIG. 11 illustrates an eleventh embodiment of an electrode array according to the present invention.

FIG. 11 illustrates an eleventh embodiment of a pacing electrode array according to the present invention. Electrodes 172, 174, 176 and 178 are located on surface 170. Surface 170 may be either a surface of an IPG or ICD, generally as in FIG. 3, or may be an electrode pad on a subcutaneous lead as in FIGS. 1 and 2. In this embodiment the physician can select any three of the electrodes to provide any of four different shielded dipole configurations to adjust the field distribution and location. Alternatively, the physician can simply select two or more electrodes on surface 170 and their associated pulse voltages to provide a variety of electrical field orientations.

In conjunction with the embodiments discussed above, one or more pairs of electrodes associated with the devices may be employed to provide prepulse inhibition. As described in U.S. Pat. No. 6,711,442 issued to Swerdlow et al. and incorporated herein by reference, a perceptible but non-painful stimulus pulse, delivered 30-500 milliseconds before a painful stimulus pulse can reduce the perceived pain associated with the painful stimulus. In the context of the present invention, prepulse inhibition may be provided by delivering a perceptible but sub-pacing threshold pulse (prepulse), 30-500 milliseconds prior to the scheduled pacing pulse. It may be preferable to use electrodes other than those employed for sensing to deliver the prepulse, as residual polarization on the electrodes delivering the prepulse my interfere with their ability to respond to cardiac depolarization signals. In this context, prepulses could be delivered either using the cardioversion/defibrillation electrodes or perhaps less preferably using non-sensing electrodes within the pacing electrode array. The parameters of the prepulses (amplitude, pulse width and/or timing) would have to be determined by the physician based upon the patient's pacing threshold and response to the prepulse stimulation. Other additional mechanisms for reducing pain associated with subcutaneous pacing, including neurostimulation and drug delivery are described below in conjunction with FIGS. 14 and 15.

In the descriptions of the pacing pulses delivered using the pacing electrode arrays described above, energy delivered to the various electrodes was regulated by varying the voltage differentials between the electrodes during the pacing pulses. While this is the simplest way to accomplish pulse energy control, alternative mechanisms, well known to the art may be substituted, including regulation of pulse current levels and, where differential energy delivery to different electrode pairs is not required, by regulation of pulse width to all electrodes.

Figure 12:
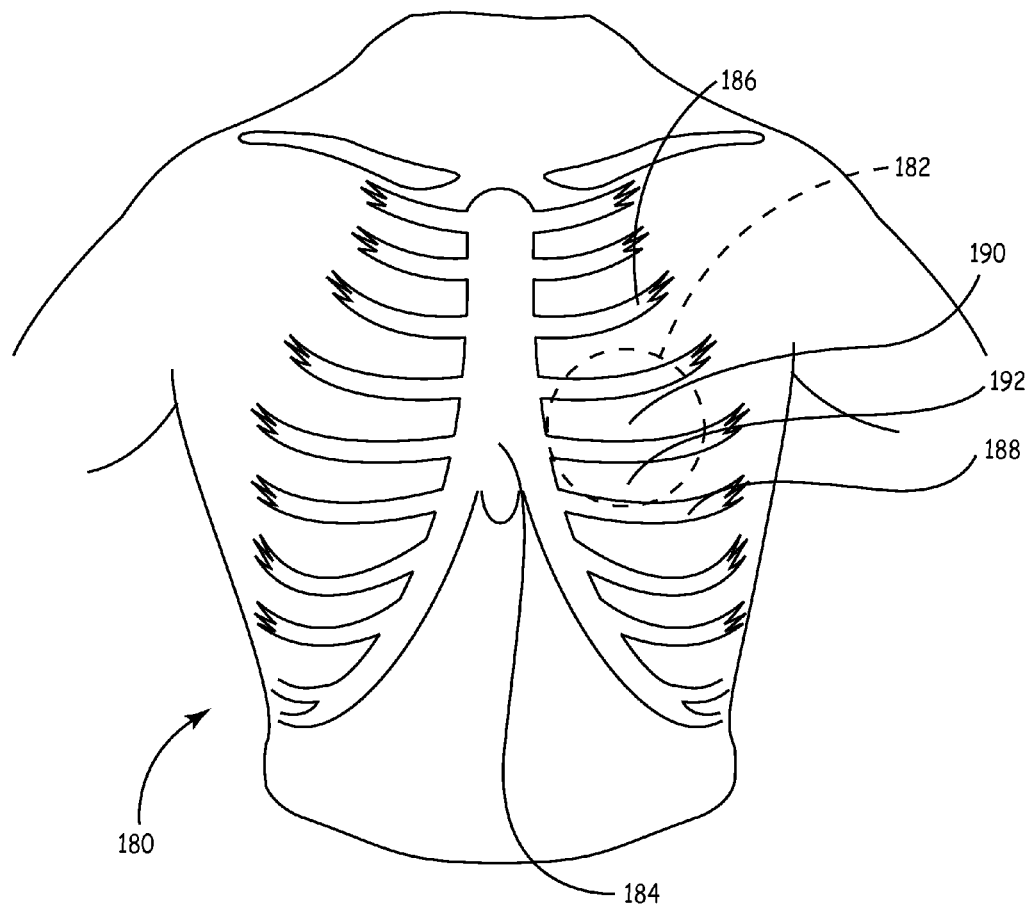
FIG. 12 illustrates the preferred implant site for an electrode array according to the present invention.

FIG. 12 is a simplified view of the anatomy of the human thorax 180, illustrating the preferred implant site for pacing electrode arrays according to the present invention. The preferred implant site 182 is located generally to the left of the midline of the sternum 184, between the third and sixth ribs 186 and 188, most preferably over the fourth or fifth intercostal spaces 190 and 192. Electrodes placed in this region are as close to the heart as possible, absent entry into the thoracic cavity. Further, they are desirably remote from the phrenic nerve, minimizing the likelihood of diaphragmatic stimulation. While it is anticipated that the primary method of implant of the pacing electrode array will be subcutaneous, external to the ribs, it is possible that in some cases the electrode array might be implanted beneath the ribs and sternum.

Figure 13:
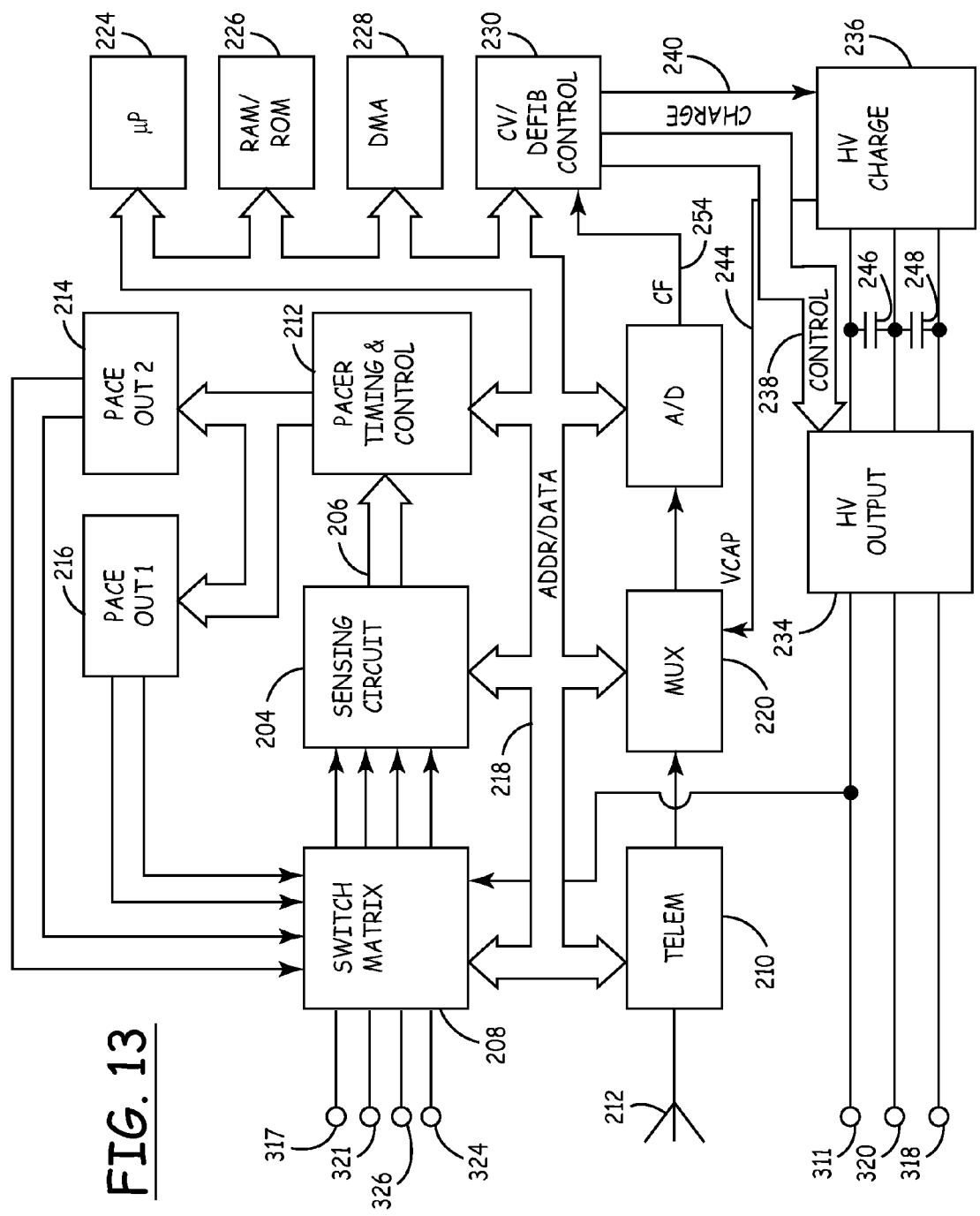
FIG. 13 illustrates an exemplary ICD which can be used with an electrode array according to the present invention.

FIG. 13 is a functional schematic diagram of an implantable pacemaker/cardioverter/defibrillator (ICD) in which the present invention may usefully be practiced. This diagram should be taken as exemplary of the type of device in which the invention may be embodied, and not as limiting, as it is believed that the invention may usefully be practiced in a wide variety of device implementations, including devices providing therapies for treating atrial arrhythmias instead of or in addition to ventricular arrhythmias. Pacemakers which do not provide anti-tachycardia pacing therapies, and anti-tachycardia pacers which do not provide cardioversion or defibrillation. Most of the components of the ICD as illustrated correspond to those used in prior art Medtronic implantable defibrillators. In particular, reference is made to the above-cited Heinrich et al. and Olson applications, as well as to US Patent Application Publication No. 20010034539 by Olson et al., also incorporated herein by reference in its entirety.

While the circuitry described above is based upon implantable device circuitry, similar circuitry would be used in those embodiments in which the invention is practiced as an external pacemaker or defibrillator, coupled to a subcutaneous electrode array or an external electrode array according to the present invention.

The device is provided with electrodes, which may be as illustrated in any of FIGS. 1-11. Alternate lead systems embodying the invention may also be substituted. The functions of the illustrated electrodes are as follows: Electrode 311 is a first defibrillation/cardioversion electrode and corresponds to electrodes 11, 31 or 52, located on the device housings in FIGS. 1-3. Electrode 320 is a second cardioversion/defibrillation electrode and corresponds to the lead mounted cardioversion/defibrillation electrodes 24 or 44 of FIGS. 1 and 2 or to electrode 54 of FIG. 3. Electrode 318 corresponds to the optional third defibrillation electrode referred to in conjunction with FIGS. 1 and 2. Electrodes 317, 321, 324 and 326 correspond to the pacing electrode array electrodes in any of FIGS. 1 to 11. As such, there may be more or less than the four electrodes illustrated, which are intended to merely be exemplary. One or more of these electrodes may be used for sensing cardiac depolarization signals.

Electrodes 311, 318 and 320 are coupled to high voltage output circuit 234. Electrodes 317, 321, 324 and 326 are coupled to switch matrix 208, which under control of Microprocessor 224 selectively couples them to sensing circuit 204 and/or to pacing output circuits 216 and 214. Sensing circuit 204 preferably takes the form of one or more automatic gain controlled amplifiers providing adjustable sensing threshold as a function of the measured depolarization wave amplitudes. Additional filtering and signal processing capabilities may be provided to allow discrimination between atrial and ventricular depolarizations. However, in the illustrated embodiment it should be understood that only ventricular signals will be of interest. A signal is provided to pacer timing and control circuitry 212 when a sensed signal or signals indicate occurrence of a cardiac depolarization. The general operation of the sensing circuit 204, in embodiments in which ventricular signals are those of interest, may correspond to that disclosed in U.S. Pat. No. 5,117,824, by Keimel et al., issued Jun. 2, 1992, for an Apparatus for Monitoring Electrical Physiologic Signals, incorporated herein by reference in its entirety. Amplifier gain would have to be increased as compared to devices employing electrodes directly contacting the heart. Alternatively, amplifiers more closely resembling those used in the Medtronic Reveal TM subcutaneous monitor, as discussed in the Heinrich et al. application cited above or in automatic external defibrillators might be substituted.

Signals from sensing circuit 204 may also be provided to multiplexer 220, and thereafter converted to multi-bit digital signals by A/D converter 222, for storage in RAM/ROM 226 under control of direct memory access circuit 228. Microprocessor 224 may employ digital signal analysis techniques to characterize the digitized signals stored in random access memory 226 to recognize and classify the patient's heart rhythm employing any of the numerous signal processing methodologies known to the art.

Control of the ICD by the physician or by a patient is accomplished via telemetry circuit 210. Externally generated programming signals are received by antenna 212, demodulated by telemetry circuitry 210 and passed through multiplexer 220 to the microprocessor via bus 218. The telemetry circuitry may be any conventional telemetry circuit employed in prior art implantable pacemakers and defibrillators and may correspond to that described in U.S. Pat. No. 5,7572,977 issued to Grevious, et al. or to U.S. Pat. No. 5,999,857 issued to Weijand, et al, both of which are included by reference in their entireties.

The remainder of the circuitry is dedicated to the provision of cardiac pacing, cardioversion and defibrillation therapies, and, for purposes of the present invention may correspond generally to circuitry known in the prior art. An exemplary apparatus is disclosed of accomplishing pacing, cardioversion and defibrillation functions follows. The pacer timing/control circuitry 212 includes programmable digital counters which control the basic rime intervals associated-with single chamber anti-bradycardia pacing, typically ventricular pacing. Circuitry 212 also controls escape intervals associated with single chamber anti-tachyarrhythmia pacing, also typically ventricular pacing, employing any anti-tachyarrhyrhmia pacing therapies known to the art. Alternative embodiments in which atrial cardioversion/defibrillation and/or atrial anti-tachycardia pacing are also believed to be within the scope of the invention.

Intervals defined by pacing circuitry 212 typically include ventricular pacing escape intervals, the refractory periods during which sensed P-waves and R-waves are ineffective to restart timing of the escape intervals and the pulse widths of the pacing pulses. The durations of these intervals are determined by microprocessor 224, in response to stored data in memory 226 and are communicated to the pacing circuitry 212 via address/data bus 218. Pacer circuitry 212 also determines the amplitude of the cardiac pacing pulses under control of microprocessor 224.

During pacing, the escape interval counters within pacer timing /control circuitry 212 are typically reset upon sensing of R-waves as indicated by signals on bus 206, and in accordance with the selected mode of pacing on timeout trigger generation of pacing pulses by pacer output circuits 214 and/ or and 216, which are coupled to programmably coupled to pairs of electrodes selected from electrodes 317, 321, 324 and 326. Output circuits 214 and 216 may correspond to conventional cardiac pacing output circuits, with the exception that they provide pulses of higher amplitude, e.g. up to 20 volts or higher or up to 35 milliamps or higher. Alternatively, output circuits 214 and 216 may correspond generally to that disclosed in U.S. Pat. No. 4,349,030, which employs a long duration pacing pulse to reduce pain associated with transcutaneous pacing or to that disclosed in U.S. Pat. No. 5,018,522 issued to Mehra, which employs a ramped pacing pulse to reduce pain associated with transcutaneous pacing. Output circuits 214 and/or 216 may also provide pacing pulses of different amplitudes to different pairs or sets of electrodes, under control of microprocessor 224, as discussed above in conjunction with the use of steering electrodes or in conjunction with other electrode configurations employing multiple electrode pairs.

The escape interval counters are also reset on generation of pacing pulses, and thereby control the basic timing of cardiac pacing functions, including anti-tachyarrhythmia pacing. The durations of the intervals defined by the escape interval timers are determined by microprocessor 224, via data/address bus 218. The value of the count present in the escape interval counters when reset by sensed R-waves and P-waves may be used to measure the durations of R-R, which measurements are stored in memory 226 and used in conjunction with the present invention to diagnose the occurrence of a variety of tachyarrhythmias Microprocessor 224 operates as an interrupt driven device, and is responsive to interrupts from pacer timing/control circuitry 212 corresponding to the occurrences of sensed R-waves and corresponding to the generation of cardiac pacing pulses. These interrupts are provided via data/address bus 218. Any necessary mathematical calculations to be performed by microprocessor 224 and any updating of the values or intervals controlled by pacer timing/control circuitry 212 take place following such interrupts. A portion of the memory 226 may be configured as a plurality of recirculating buffers, capable of holding series of measured intervals, which may be analyzed in response to the occurrence of a pace or sense interrupt to determine whether the patient's heart is presently exhibiting ventricular tachyarrhythmia.

The arrhythmia detection method of the present invention may include any workable prior art tachyarrhythmia detection algorithms. For example, The detection algorithms proposed in the various patents cited in the background of the invention section might be employed. Alternatively the ventricular arrhythmia detection methodology of presently available Medtronic pacemaker/cardioverter/defibrillators, as describe in the above-cited Olson et al. applications may be employed.

In the event that a ventricular tachyarrhythmia is detected, and an anti-tachyarrhythmia pacing regimen is desired, appropriate timing intervals for controlling generation or anti-tachyarrhythmia pacing therapies are loaded from microprocessor 224 into the pacer timing and control circuitry 212, to control the operation of the escape interval counters therein and to define refractory periods during which detection of R-waves and P-waves is ineffective to restart the escape interval counters.

In the event chat generation of a cardioversion or defibrillation pulse is required, microprocessor 224 employs the escape interval counter to control timing of such cardioversion and defibrillation pulses, as well as associated refractory periods. In response to the detection of atrial or ventricular fibrillation or tachyarrhythmia requiring a cardioversion pulse, microprocessor 224 activates cardioversion/defibrillation control circuitry 230, which initiates charging of the high voltage capacitors 246, 248 via charging circuit 236, under control of high voltage charging control line 240. The voltage on the high voltage capacitors is monitored via VCAP line 244, which is passed through multiplexer 220 and in response to reaching a predetermined value set by microprocessor 224, results in generation of a logic signal on Cap Full (CF) line 254, terminating charging. Thereafter, timing of the delivery of the defibrillation or cardioversion pulse is controlled by pacer timing/control circuitry 212. Following delivery of the fibrillation or tachycardia therapy the microprocessor then returns the device to cardiac pacing and awaits the next successive interrupt due to pacing or the occurrence of a sensed atrial or ventricular depolarization.

One embodiment of an appropriate system for delivery and synchronization of ventricular cardioversion and defibrillation pulses and for controlling the timing functions related to them is disclosed in more detail in commonly assigned U.S. Pat. No. 5,188,105 by Keimel, issued Feb. 23, 1993, and incorporated herein by reference in its entirety. However, any known cardioversion or defibrillation pulse control circuitry is believed usable in conjunction with the present invention. In the illustrated device, delivery of the cardioversion or defibrillation pulses is accomplished by output circuit 234, under control of control circuitry 230 via control bus 238. Output circuit 234 determines whether a monophasic or biphasic pulse is delivered, whether the housing 311 serves as cathode or anode and which electrodes are involved in delivery of the pulse. An example of output circuitry for delivery of biphasic pulse regimens may be found in U.S. Pat. No. 4,727,877, incorporated by reference in its entirety.

An example of circuitry which may be used to control delivery of monophasic pulses is set forth in commonly assigned U.S. Pat. No. 5,163,427, by Keimel, issued Nov. 17, 1992, also incorporated herein by reference in its entirety. However, output control circuitry as disclosed in U.S. Pat. No. 4,953,551, issued to Mehra et al. on Sep. 4, 1990 or U.S. Pat. No. 4,800,883, issued to Winstrom on Jan. 31, 1989 both incorporated herein by reference in their entireties, may also be used in conjunction with a device embodying the present invention for delivery of biphasic pulses.

In modern implantable cardioverter/defibrillators, the particular therapies are programmed into the device ahead of time by the physician, and a menu of therapies is typically provided. For example, on initial detection of a tachycardia, an anti-tachycardia pacing therapy may be selected and delivered to the pacing electrode array. On redetection of tachycardia, a more aggressive anti-tachycardia pacing therapy may be scheduled. If repeated attempts at anti-tachycardia pacing therapies fail, a higher level cardioversion pulse may be selected thereafter. Therapies for tachycardia termination may also vary with the race of the detected tachycardia, with the therapies increasing in aggressiveness as the rate of the detected tachycardia increases. For example, fewer attempts at antitachycardia pacing may be undertaken prior to delivery of cardioversion pulses if the rate of the detected tachycardia is above a preset threshold. The references cited above in conjunction with descriptions of prior art tachycardia detection and treatment therapies are applicable here as well.

In the event that fibrillation is identified, the typical therapy will be delivery of a high amplitude defibrillation pulse, typically in excess of 5 joules. Lower energy levels may be employed for cardioversion. As in the case of currently available implantable pacemaker/cardioverter/defibrillators, and as discussed in the above-cited references, it is envisioned that the amplitude of the defibrillation pulse may be incremented in response to failure of an initial pulse or pulses to terminate fibrillation. Prior art patents illustrating such preset therapy menus or anti-tachyarrhythmia therapies include U.S. Pat. No. 4,830,006, issued to Haluska et al., U.S. Pat. No. 4,727,380, issued to Vollmann et al. and U.S. Pat. No. 4,587, 970, issued to Holley et al., all also incorporated herein by reference in their entireties.

The device illustrated in FIG. 13 provides the full functionality of a modern ICD. If the invention is to be practiced in an embodiment wherein no high voltage cardioversion/defibrillation pulses are to be delivered, such in cases in which the pacing electrode array is coupled to an external or implantable pacemaker, the structures in FIG. 13 associated with delivery of cardioversion/defibrillation pulses can be deleted. Provisions for detection of tachyarrhythmias should be retained if the pacemaker is to provide anti-arrhythmia pacing.

Figure 14:
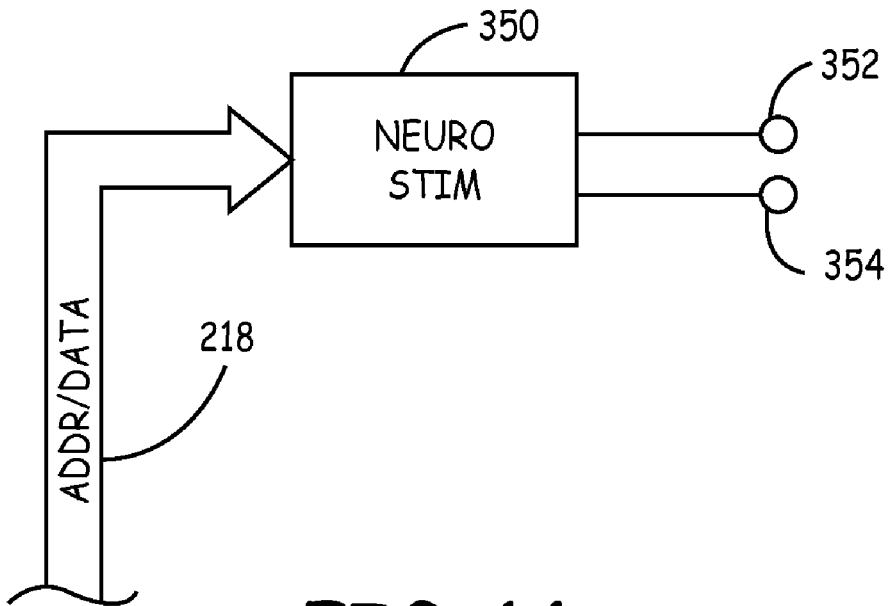
FIG. 14 illustrates an optional neurostimulator which may be incorporated in the ICD of FIG. 13.

FIG. 14 illustrates the optional addition of a neurostimulator to the ICD illustrated in FIG. 13. Neurostimulator 350 is a conventional neurostimulation output circuit, such as that employed in Medtronic Itrel™ spinal cord stimulators, operated under control of microprocessor 224 (FIG. 13) via bus 218. Neurostimulation pulses for pain control are may be generated by stimulator 350 continuously in response to subcutaneous pacing functions being enabled Alternatively neurostimulation might be triggered only in response to the attainment of a preset level of pacing pulse delivery, e.g. a preset number of pulses per hour. In an additional alternative embodiment, neurostimulation may be triggered in response to a signal from an external programmer provided to the patient, if pacing is becoming frequent and painful. Neurostimulation pulses are delivered to electrodes 352 and 354, which are preferably separate from the pacing electrode array and may be located subcutaneously or intra-spinally at about the T1-T4 region as described in U.S. Pat. No. 5,662,689 issued to Elsberry et al., incorporated herein by reference in its entirety, or at such other location determined to be effective in reducing pain associated with subcutaneous pacing. Use of the same electrodes employed for pacing to deliver neurostimulation, as disclosed in U.S. Pat. No. 5,782,882 issued to Lehman might be possible in some embodiments, but may interfere with their ability to be used for sensing of cardiac depolarizations.

If the invention is embodied as an ICD or implantable pacemaker, as described above, the neurostimulation circuitry will most likely be included in the device housing as part of the device circuitry. Location of the neurostimulation circuitry in a separate housing, however is believed to be within the scope of the invention. If the invention is embodied as an external stimulator, coupled to an implantable electrode array or an array applied to the skin, the neurostimulation circuitry may be incorporated in the device circuitry as described above or may be an add-on cassette. In these cases, the neurostimulation electrodes may be located subcutaneously or externally to deliver transcutaneous nerve stimulation.

Figure 15:
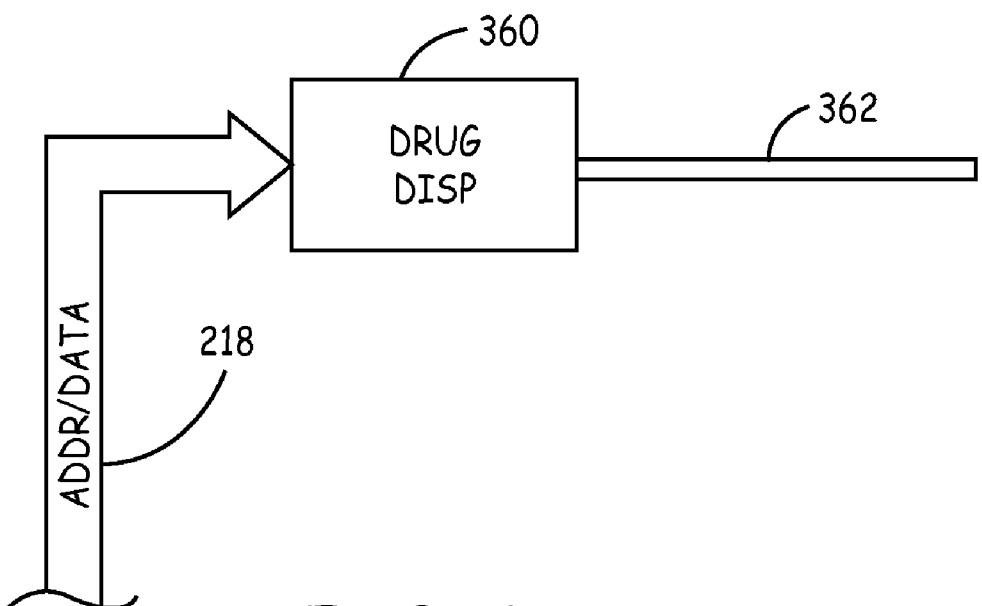
FIG. 15 illustrates an optional drug dispenser which may be incorporated in the ICD of FIG. 13.

FIG. 15 illustrates the optional addition of an analgesic drug dispenser to the ICD illustrated in FIG. 13. Drug dispenser 360 is a conventional implantable drug dispensing pump with associated drug reservoir, such as that employed in the Medtronic Synchromed™ drug dispenser, operated under control of microprocessor 224 (FIG. 13) via bus 218. Delivery of analgesic drugs for pain control may be provided by dispenser 360 continuously in response to subcutaneous pacing functions being enabled. Alternatively drug delivery might be triggered only in response to the attainment of a preset level of pacing pulse delivery, e.g. a preset number of pulses per hour. In an additional alternative embodiment, drug delivery may be triggered in response to a signal from an external programmer provided to the patient, if pacing is becoming frequent and painful. An analgesic drug is provided to catheter 362 which may be located intra-spinally at about the T1-T4 region as described in U.S. Pat. No. 5,662,689 issued to Elsberry et al., cited above, or at such other location determined to be effective in reducing pain associated with subcutaneous pacing.

If the invention is embodied as an ICD or implantable pacemaker, as described above, the drug dispenser may be included in the device housing as described above. Location of the drug dispenser in a separate housing, however is believed to be within the scope of the invention. If the invention is embodied as an external stimulator, coupled to an implantable electrode array or an array applied to the skin, the drug dispenser may be incorporated in the device as described above or may be an add-on cassette. In these cases, the drug delivery catheter will pass through the skin to the desired delivery site.

In conjunction with either nerve stimulation or delivery of an analgesic it should be considered that there is generally a significant time lag between initiation of the pain control therapy and actual results. This factor may limit the number of patients in whom intermittent activation of these pain control therapies is employed.

In conjunction with the above specification.

What is claimed is:

1. A cardiac pacemaker, comprising:
a pacing electrode array comprising an outer ring electrode and a central electrode located concentric to the outer ring electrode and a first steering electrode laterally offset from the outer ring and central electrodes; and
pacing pulse generator means for delivering pacing pulses to the outer ring and central electrodes with the outer ring and central electrodes at differing polarities and to the first steering electrode at the same polarity as one of the outer ring and central electrodes, wherein the pacemaker is an implantable pacemaker having a device housing and wherein the pacing electrode array is located on the device housing.

2. A cardiac pacemaker, comprising:
a pacing electrode array comprising an outer ring electrode and a central electrode located concentric to the outer ring electrode and a first steering electrode laterally offset from the outer ring and central electrodes; and
pacing pulse generator means for delivering pacing pulses to the outer and central electrodes with the outer and ring electrodes at differing polarities and to the first steering electrode at the same polarity as one of the outer ring and central electrodes, wherein the pacemaker is an external pacemaker provided with an external lead and wherein the pacing electrode array is located on the external lead and is configured to be located on a skin surface of a patient for delivering the pacing pulses to a heart of the patient.

3. A cardiac pacemaker, comprising:
a pacing electrode array comprising two concentric ring electrodes and a central electrode located concentric to the ring electrodes;
an electrode selector operable to select two electrodes within the electrode array; and
pacing pulse generator means for delivering pacing pulses to the selected electrodes with the selected electrodes at differing polarities, wherein the pacemaker is an implantable pacemaker having a device housing and wherein the pacing electrode array is located on the device housing.

4. A pacemaker according to claim 3, wherein the pacemaker further comprises means for adjusting pacing pulse energy delivered between pairs of electrodes within the pacing electrode array.

5. A cardiac pacemaker, comprising:

a pacing electrode array comprising two concentric ring electrodes and a central electrode located concentric to the ring electrodes;

an electrode selector operable to select two electrodes within the electrode array; and pacing pulse generator means for delivering pacing pulses to the selected electrodes with the selected electrodes at differing polarities, wherein the pacemaker is an external pacemaker provided with an external lead and wherein the pacing electrode array is located on the external lead and is configured to be located on a skin surface of a patient for delivering the pacing pulses to a heart of the patient.

* * * * *

UNITED STATES PATENT AND TRADEMARK OFFICE
CERTIFICATE OF CORRECTION

PATENT NO. : 7,496,408 B2  Page 1 of 1
APPLICATION NO. : 11/004498
DATED : February 24, 2009
INVENTOR(S) : Raja N. Ghanem It is certified that error appears in the above-identified patent and that said Letters Patent is hereby corrected as shown below:

On title page Item [54] - delete "Electrodes Array for A Pacemaker" and insert in place thereof --An Electrode Array for a Pacemaker--.

Signed and Sealed this

Eighteenth Day of August, 2009

David J. Kappos
*Director of the United States Patent and Trademark Office*

UNITED STATES PATENT AND TRADEMARK OFFICE
CERTIFICATE OF CORRECTION

PATENT NO. : 7,496,408 B2  
APPLICATION NO. : 11/004498  
DATED : February 24, 2009  
INVENTOR(S) : Raja N. Ghanem Page 1 of 1

It is certified that error appears in the above-identified patent and that said Letters Patent is hereby corrected as shown below:

On title page Item [54] and Column 1, line 1 - delete "Electrodes Array for A Pacemaker" and insert in place thereof --An Electrode Array for a Pacemaker--.

This certificate supersedes the Certificate of Correction issued August 18, 2009.

Signed and Sealed this

Eighth Day of September, 2009

David J. Kappos  
*Director of the United States Patent and Trademark Office*